(12) United States Patent
Zino et al.

(10) Patent No.: US 9,740,821 B2
(45) Date of Patent: Aug. 22, 2017

(54) REAL-TIME COMMUNICATION BETWEEN MEDICAL DEVICES OVER A DICOM NETWORK

(71) Applicant: BIOSENSE WEBSTER (ISRAEL) LTD., Yokneam (IL)

(72) Inventors: Eliahu Zino, Atlit (IL); Matityahu Amit, Kohav-Yair-Zur-Yigal (IL); Gil Zigelman, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 377 days.

(21) Appl. No.: 14/138,591

(22) Filed: Dec. 23, 2013

(65) Prior Publication Data

US 2015/0178448 A1  Jun. 25, 2015

(51) Int. Cl.
G06F 19/00 (2011.01)
A61B 6/00 (2006.01)
A61B 8/00 (2006.01)

(52) U.S. Cl.
CPC ............ *G06F 19/321* (2013.01); *A61B 6/487* (2013.01); *A61B 6/542* (2013.01); *A61B 6/547* (2013.01); *A61B 8/4245* (2013.01); *G06F 19/30* (2013.01); *G06F 19/32* (2013.01); *G06T 2207/10064* (2013.01); *G06T 2207/10121* (2013.01)

(58) Field of Classification Search
CPC ....... A61B 5/06; A61B 8/4245; A61B 8/4254; A61B 6/487; A61B 6/542; A61B 6/547; G06T 2207/10064; G06T 2207/10116; G06T 2207/10121; G06F 19/30; G06F 19/32; G06F 19/321

USPC ........... 340/870.01, 870.02, 870.07
See application file for complete search history.

(56) References Cited

U.S. PATENT DOCUMENTS

| | | | |
|---|---|---|---|
| 2002/0058868 A1 | 5/2002 | Hoshino et al. | |
| 2002/0085681 A1* | 7/2002 | Jensen | A61B 5/06 378/197 |
| 2004/0019447 A1 | 1/2004 | Shachar | |
| 2004/0076259 A1* | 4/2004 | Jensen | A61B 6/12 378/91 |
| 2005/0063575 A1* | 3/2005 | Ma | G06F 17/30265 382/128 |
| 2007/0030957 A1 | 2/2007 | Pommi | |
| 2008/0095421 A1 | 4/2008 | Sun et al. | |

(Continued)

FOREIGN PATENT DOCUMENTS

EP  1868311 A1  12/2007

OTHER PUBLICATIONS

European Search Report received Jun. 25, 2015 for Application No. EP14199772.

(Continued)

*Primary Examiner* — Amine Benlagsir
*Assistant Examiner* — Franklin Balseca
(74) *Attorney, Agent, or Firm* — Louis J. Capezzuto (57) ABSTRACT

A method includes sending from a first medical device to a second medical device a request for data using a communication protocol that includes messages for conveying medical measurement results. In response to the request, at least one message is produced in the second medical device that includes the requested data and a dummy payload instead of the medical measurement results, and the at least one message is sent from the second medical device to the first medical device using the communication protocol.

16 Claims, 3 Drawing Sheets

(56) References Cited

U.S. PATENT DOCUMENTS

| | | | |
|---|---|---|---|
| 2009/0306509 A1* | 12/2009 | Pedersen | G01S 15/8936 600/446 |
| 2011/0176803 A1* | 7/2011 | Song | H04B 10/116 398/43 |
| 2013/0163835 A1 | 6/2013 | Park | |
| 2013/0241801 A1* | 9/2013 | Petrik | G06F 3/1423 345/1.1 |
| 2014/0187915 A1* | 7/2014 | Yaroshenko | A61B 5/062 600/424 |

OTHER PUBLICATIONS

Abdala, D.D. et al. Application Protocol for a DICOM Real Time Collaborative System. IEEE Computer Society, Proceedings of The 19$^{th}$ IEEE Symposium on Computer-Based Medical Systems (CBMS'06) 2006.

Wagenheim, Aldo Von et al. Recording and Reenactment of Collaborative Diagnosis Sessions Using DICOM. Journal of Digital Imaging, vol. 22, No. 6 Dec. 2009, pp. 605-619.

* cited by examiner

REAL-TIME COMMUNICATION BETWEEN MEDICAL DEVICES OVER A DICOM NETWORK

FIELD OF THE INVENTION

The present invention relates generally to medical devices, and particularly to methods and systems for communication between medical devices.

BACKGROUND OF THE INVENTION

Digital Imaging and Communications in Medicine (DICOM) is a standard used in medical imaging. The DICOM standard comprises a data file format and a network communication protocol for transmitting medical imaging data between medical devices. DICOM is specified, for example, in a standard entitled "Digital Imaging and Communications in Medicine (DICOM)," published by the National Electrical Manufacturers Association (NEMA), 2011, which is incorporated herein by reference.

SUMMARY OF THE INVENTION

An embodiment of the present invention provides a method including sending from a first medical device to a second medical device a request for data using a communication protocol that includes messages for conveying medical measurement results. In response to the request, at least one message is produced in the second medical device that includes the requested data and a dummy payload instead of the medical measurement results, and the at least one message is sent from the second medical device to the first medical device using the communication protocol.

In some embodiments, sending the request includes opening at least one association between the first medical device and the second medical device, and sending the at least one message includes sending the data in multiple messages in response to the request while the at least one association is open. In other embodiments, sending the request includes opening at least one association between the first medical device and the second medical device, and sending the at least one message includes sending the data in one or more bursts while the at least one association is open.

In some embodiments, the communication protocol includes a Digital Imaging and Communications in Medicine (DICOM) protocol. In other embodiments, the first medical device includes a position tracking system. In yet other embodiments, the second medical device includes a fluoroscopic imaging system.

In some embodiments, the medical measurement results include an image, and the dummy data includes a dummy image. In other embodiments, the first medical device includes a position tracking system, the second medical device includes a fluoroscopic imaging system, and sending the at least one message includes sending one or more messages that report respective spatial positions of the fluoroscopic imaging system.

In some embodiments, the method includes presenting the reported positions of the fluoroscopic imaging system to an operator, using the position tracking system, without activating the fluoroscopic imaging system. In other embodiments, the method includes compensating, based on the reported positions, for a distortion caused by the fluoroscopic imaging system to a magnetic field of the position tracking system.

There is also provided, in accordance with an embodiment of the present invention, a system including a first medical device and a second medical device. The first medical device is configured to send a request for data using a communication protocol that includes messages for conveying medical measurement results. The second medical device is configured to produce, in response to the request, at least one message that includes the requested data and a dummy payload instead of the medical measurement results, and to send the at least one message to the first medical device using the communication protocol.

The present invention will be more fully understood from the following detailed description of the embodiments thereof, taken together with the drawings in which:

DETAILED DESCRIPTION OF EMBODIMENTS

Overview

Medical communication networks are used, for example, for connecting imaging devices (e.g., fluoroscopic imaging systems) with servers, data storage devices, scanners, printers and other network peripherals. Some medical communication networks use the Digital Imaging and Communications in Medicine (DICOM) protocol, cited above. In conventional DICOM operation, at least one association is opened between medical devices over the network, the requested data is sent, and the association is then closed. The payload of a DICOM message may comprise various kinds of medical measurement data, such as fluoroscopic images or electrocardiograms.

Embodiments of the present invention that are described herein provide improved methods and systems for communication between medical devices. The disclosed techniques use a protocol such as DICOM, which specifies transfer of images and other non-real-time medical measurements, for transferring real-time data.

In some embodiments, one medical device sends a request for real-time data to a second medical device. In response to the request, the second medical device constructs a DICOM message that comprises the requested data. In the field or tag of the message that is intended for conveying medical measurement data, the second device inserts a small-size dummy payload. The resulting message is small in size and thus suitable for real-time messaging.

In some embodiments, the second medical device sends the requested data in a sequence of messages in response to a single request. The association between the two medical devices is kept open during the entire sequence, rather than closing and re-opening the association for each message. This feature further reduces the messaging overhead and latency, and therefore improves real-time performance.

In one example embodiment, the first medical device comprises a magnetic position tracking system, and the second medical device comprises a fluoroscopic imaging system. In this embodiment, the fluoroscopic imaging system sends to the magnetic position tracking system a series of messages, which report the spatial position of the fluoroscopic imaging system in real time. The magnetic position tracking system may use this real-time data, for example, to position the fluoroscopic imaging system properly without irradiating the patient, and/or to compensate for metal interference caused by the fluoroscopic imaging system to the magnetic field of the magnetic position tracking system.

The methods and systems described herein enable medical devices to communicate with one another in real time using a non-real-time protocol such as DICOM. These techniques can be used with legacy DICOM-based systems or networks, with little or no modification to DICOM infrastructure (e.g., DICOM drivers and communication software in the medical devices).

System Description

Figure 1:
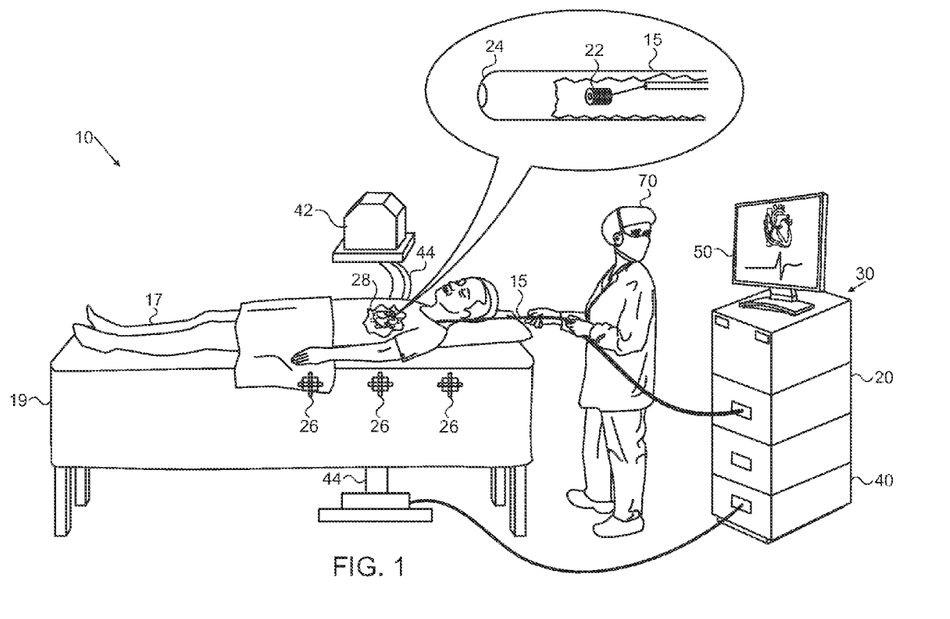
FIG. 1 is a schematic, pictorial illustration of an intrabody probe tracking and imaging system, in accordance with an embodiment of the present invention.

FIG. 1 is a schematic, pictorial illustration of an intra-body tracking and imaging system 10, in accordance with an embodiment of the present invention. An intra-body probe, such as a catheter 15, is connected to a position tracking system, also referred to as a catheter tracking system (CTS) 20, in a console 30 and inserted percutaneously into a living body 17 of a patient laying on a table, or gurney 19. Catheter 15 comprises a magnetic sensor coil 22 at a distal tip 24, which is navigated into an organ, such as a heart 28 of the patient.

In some embodiments as shown in FIG. 1, CTS 20 comprises one or more magnetic field generators 26, which generate a magnetic field through the body of the patient. The magnetic field induces electrical signals in catheter magnetic sensor coil 22. Field generators 26, which are also referred to as location pads, or transmitter location pads, may be located under the patient. The induced electrical signals in catheter magnetic sensor coil 22 are used by CTS 20 to track and locate the position of sensor 22, and thus the catheter distal tip, in patient 17. The tracked position of the catheter distal tip is typically displayed to an operator 70 on an output display monitor 50.

In other embodiments, non-magnetic catheter tracking based on impedance measurements may be used. In this case, CTS 20 is configured to drive and measure a plurality of currents between one or more electrodes disposed near distal tip 24 on the body of catheter 15, and one or more skin patch electrodes (not shown in the figure). CTS 20 uses the measured currents to compute a plurality of impedances which are used to locate the position of distal tip 24 of catheter 15 in patient body 17.

In some therapeutic and diagnostic medical procedures, CTS 20 is used in conjunction with an imaging system such as a fluoroscopic imaging system (FIS) 40 in console 30. A fluoroscopic image of the heart, or any other suitable region of interest in the body, is acquired by a fluoroscope 42 connected to FIS 40 as shown in FIG. 1.

Fluoroscope 42 is mounted above patient 17 and rotates around the patient on a C-arm gantry 44. The fluoroscopic image of the heart can be viewed on display 50 by operator 70. Display 50 may comprise a separate display each for FIS 40 and CTS 20, or a common display for both FIS 40 and CTS 20. Examples of a magnetic tracking and three-dimensional (3D) mapping system 20 shown in FIG. 1, are the CARTO and CARTO3 systems (Biosense Webster, Diamond Bar, Calif.).

The system configuration as shown in FIG. 1 is an exemplary configuration, which is shown purely for the sake of visual clarity. Any suitable configuration of system 10 may be used and implemented.

In some embodiments, FIS 40 and CTS 20 communicate with one another using the DICOM protocol, cited above. Although the embodiments described herein refer mainly to DICOM, the disclosed techniques can be used with any other suitable communication protocol.

DICOM is a well-established protocol, which is used to provide communication for medical devices, for example for sending medical measurement data for storage or for display. A DICOM data item or message, as will be described in detail later, comprises medical measurement data such as an image or electrocardiogram. In addition, DICOM data items may comprise other data such as the patient's personal data and other system parameters or metadata. Additionally or alternatively, the disclosed techniques can be used for conducting real-time communication between any other suitable medical devices or systems.

Example Use Cases

One example use case of the disclosed techniques has to do with minimizing irradiation of the patient when positioning fluoroscope 42. Conventionally, operator 70 would typically require fluoroscopic images of the target region in the organ. In preparation for the procedure, the operator would locate fluoroscope 42 relative to the patient iteratively, by trial and error. In such a process, fluoroscope 42 is positioned, an image is acquired by applying radiation to the patient, and the acquired image is analyzed to assess if an image with the desired orientation was obtained. If not, fluoroscope 42 is repositioned and another image acquired. This process subjects the patient to unnecessarily high doses or radiation.

In some embodiments of the present invention, FIS 40 sends to CTS 20 a series of DICOM messages that report the real-time position of fluoroscope 42 relative to the patient. Using this real-time information, CTS 20 is able to indicate the orientation of fluoroscope 42 to operator 70 without having to irradiate the patient. Irradiation by FIS 40 is initiated only when the fluoroscope is positioned properly. As a result, patient irradiation is reduced to a minimum.

Another example use case has to do with compensating for metal distortion caused by fluoroscope 42 to the magnetic field of CTS 20. Typically, CTS 20 applies external magnetic fields (e.g., using magnetic sources 26) to the patient's body so as to induce electrical signals in sensor 22 at distal tip 24 of catheter 15. The induced electrical signals in the sensor are used by CTS 20 to identify the position of the catheter in the body. However, fluoroscope 42 usually comprises a large metallic body. The metallic body may distort the applied magnetic field generated by magnetic sources 26 of the CTS, inducing errors in the measured position of the catheter in the patient during catheter tracking.

In some embodiments of the present invention, FIS 40 sends to CTS 20 a series of DICOM messages that report the real-time position of fluoroscope 42 relative to the patient. Using the known real-time position of fluoroscope 42, CTS 20 is able to compensate for the field distortion caused by the fluoroscope. As a result, the CTS is able to track the position of catheter 22 accurately, even in the presence of the large metallic fluoroscope.

Communication Between Medical Devices Over a Network Using DICOM Protocol

Figure 2:
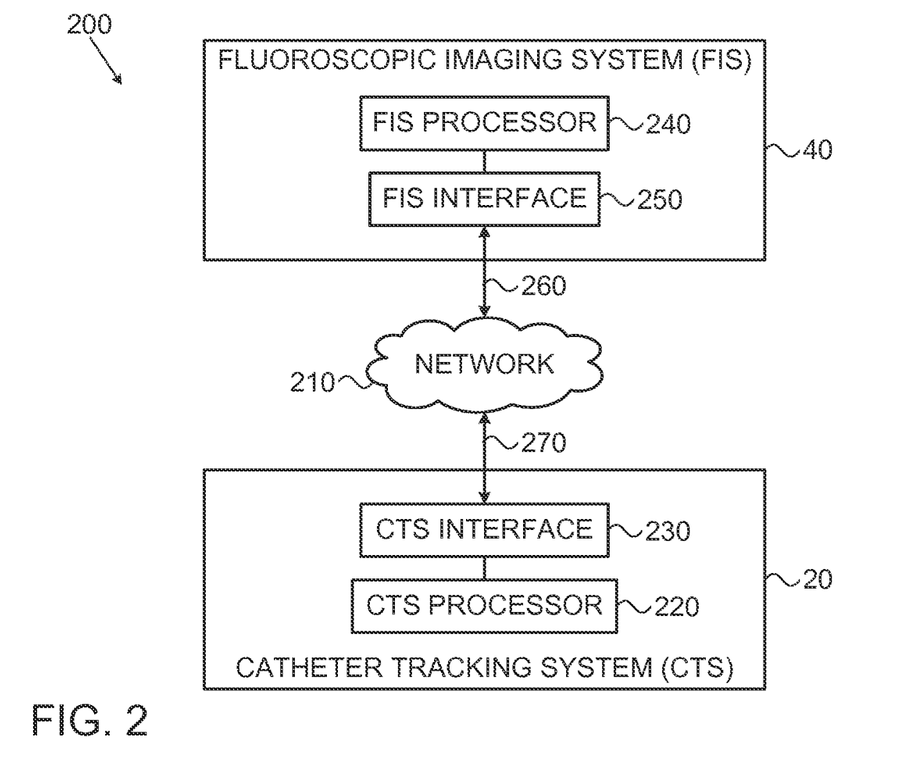
FIG. 2 is a block diagram that schematically illustrates a medical communication system, in accordance with an embodiment of the present invention.

FIG. 2 is a block diagram that schematically illustrates a medical communication system 200, in accordance with an embodiment of the present invention. In this example (which can be used for implementing system 10 of FIG. 1), CTS 20 and FIS 40 communicate with each other over a network 210. Catheter tracking system (CTS) 20 comprises a CTS processor 220 that carries out the various processing tasks of the CTS, and a CTS interface 230 that connects CTS 20 to network 210 over a data bus 270. Fluoroscopic imaging system (FIS) 40 comprises an FIS processor 240 that carries out the various processing tasks of the FIS, and an FIS interface 250 that connects FIS 40 to network 210 over a data bus 260.

FIS processor 240 and/or CTS processor 220 may be used, for example, to register the respective FIS and CTS coordinate systems to a common coordinate system (e.g., body coordinate system (BCS)). Additionally or alternatively, FIS processor 240 and CTS processor 220 may be used to establish network associations with one or more medical devices over network 210.

Some elements of FIS 40 and/or CTS 20 may be implemented in hardware, e.g., in one or more Application-Specific Integrated Circuits (ASICs) or Field-Programmable Gate Arrays (FPGAs). Additionally or alternatively, some elements of FIS 40 and/or CTS 20 can be implemented using software, or using a combination of hardware and software elements. In some embodiments, FIS processor 240 and/or CTS processor 220 comprise a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The system configuration as shown in FIG. 2 is an exemplary configuration, which is purely for the sake of conceptual clarity. Any suitable communication protocol may be used such that two or more of the medical devices communicate over network 210. Alternatively, any other suitable system configuration can be used to perform the functions of the embodiments described herein. Any suitable imaging system may be used and not limited to FIS 20.

DICOM Data Items

The DICOM messages, or data items, use a standardized format as described in the DICOM standard document cited above. The terms "message" and "data item" are used interchangeably herein. Each message comprises one or more data fields, each field with a unique attribute, or TAG. For example, TAGs may comprise the patient information, or a particular position attribute of the imaging system. Each message further comprises a field or TAG for conveying medical measurement data such as an image or electrocardiogram.

An example of a DICOM data item is shown in Table I below, with columns denoted TAG, Attribute Name, VR (value representation), and VALUE (e.g., the actual data). The DICOM data item shown in Table I is chosen merely for conceptual clarity and not by way of limitation of the embodiments of the present invention.

Table I shows only selected TAGs related to the embodiments of the present invention from among the many possible DICOM TAGs referenced in the DICOM standard document. It should also be noted that the last column in Table I denoted VALUE has the value of the parameter defined by the particular TAG. However in Table I, a description of the TAG (in brackets) in the VALUE column is given merely for reference, and not the actual value of the TAG parameter, which varies for each medical session.

The TAGs have representations listed in the DICOM standard document as referenced previously. For example, the TAG (0008,0060) is defined in the DICOM standard as the modality, or the type of imaging equipment used in the medical procedure. An example of a modality is "XA=X-Ray Angiography". Patient data is given by the set of TAGs in the format (0010,xxxx) where xxxx is any 4 digit representation in accordance with the DICOM standard.

Similarly, specific TAGs for a fluoroscopic imaging system is given by the TAG set in the format (0018,xxxx). Fluoroscope position data can be found within this TAG set. For example, TAG (0018,1111) is the "DISTANCE SOURCE TO PATIENT", or the fluoroscope distance of the source to the patient. TAG (0018,1510) is the "POSITIONER PRIMARY ANGLE", or the fluoroscope right anterior oblique (RAO)/left anterior oblique (LAO) angle of the C-arm. The image pixel data attributes are defined in the TAG set in the format (0028,xxxx) and the pixel data is given in the TAG (7FE0,0010).

The column denoted VR is the value representation, or the type of data described in the particular TAG in accordance with the TAGs as described in the DICOM standard. For the TAG shown in Table I, CS denotes Code String, PN denotes patient name, AS denotes age string, DS denotes decimal string, US denotes unsigned short and OW denotes other word string.

The DICOM communication protocol is typically based on transmission control protocol/internet protocol (TCP/IP). Conventionally, at least one network association is opened between two or more medical devices connected to the network. The DICOM data item, or message, is transmitted over the network when requested by a medical device that is connected to the network. After the data message is transferred, the network association is closed.

DICOM Message Size Reduction Using Dummy Payload

In the disclosed embodiments, a first medical device sends a request to a second medical device for data using a communication protocol such as DICOM. In response to the request, the second medical device is configured to produce at least one message with the requested data and a dummy payload. The dummy payload is inserted instead of the medical measurements (e.g., instead of a fluoroscopic image) so as to reduce the overall size of the data item and permit real-time communication. The message is then sent to the first medical device in accordance with the communication protocol.

In an example embodiment, at least one network association between the first and second medical devices is opened when the medical session is initiated, and closed only when the medical session is terminated. While the association is open, the DICOM communication protocol is used for transmitting the fluoroscope position to CTS 20 in real time as FIS 40 creates the DICOM data items. The real-time fluoroscope position data is used, for example, to correct for the distortion by metallic fluoroscope 42 on the magnetic fields generated by sources 26 in CTS 20, or for assisting operator 70 to evaluate the orientation of the fluoroscopic image in CTS 20 before radiation is applied to patient 17 by FIS 40.

If the DICOM data item were to carry a conventional fluoroscopic image file as in the TAG (7FE0,0010) shown in Table I, the DICOM data item would be very large. Transmitting such large DICOM data items from FIS 40 to CTS 20 with the fluoroscope position bundled with the image pixel data would make the data message prohibitively too long for a real time update of the position of fluoroscope 42 over the network. For example, when the pixel data represents a single fluoroscopic image, the size is typically on the order of 2-2.5 MB. In some cases, a conventional DICOM data item comprises multiple fluoroscopic images at different orientations bundled in the data item in the field with TAG (7FE0,0010).

TABLE I

DICOM data item example

| TAG | ATTRIBUTE NAME | VR | VALUE |
|---|---|---|---|
| (0008,0060) | MODALITY | CS | e.g., XA <X-Ray Angiography> |
| (0010,0010) | PATIENT NAME | PN | <patient name> |
| (0010,0030) | PATIENT BIRTH DATE | DA | <patient birthdate> |
| (0018,1110) | DISTANCE SOURCE TO DETECTOR | DS | <fluoroscope distance source to detector> |
| (0018,1111) | DISTANCE SOURCE TO PATIENT | DS | <fluoroscope distance source to patient> |
| (0018,1510) | POSITIONER PRIMARY ANGLE | DS | <fluoroscope RAO/LAO angle of C-arm> |
| (0018,1511) | POSITIONER SECONDARY ANGLE | DS | <fluoroscope cranial/caudal angle of C-arm> |
| (0028,0010) | ROWS | US | <pixel data - no. of rows> |
| (0028,0011) | COLUMNS | US | <pixel data - no. of columns> |
| (0028,0100) | BITS ALLOCATED | US | <pixel data size no. of bits allocated> |
| (7FE0,0010) | PIXEL DATA | OW | <pixel data> |

In the embodiments of the present invention, FIS processor 240 is configured to insert a dummy payload into the data item, instead of actual medical measurements, so as to reduce the size of the data item. For example, the dummy payload may comprise a dummy image whose size is 1×1 pixels inserted to the DICOM data field (e.g., TAG (7FE0, 0010) in Table I). Relative to a fluoroscopic image having a typical size of 2-2.5 MB, a dummy 1×1 pixel has a size of only 2 bytes. By using this method, the DICOM data item size is significantly reduced. Thus, real time transmission of the fluoroscope position data from FIS 40 to CTS 20 over network 210 is now possible.

To further describe the transmission of the fluoroscope position in accordance with the embodiments of the present invention using DICOM protocol-specific terminology, CTS 20 opens a first association with FIS 40 over network 210. CTS 20 sends a C_MOVE DICOM command. The C_MOVE DICOM command comprises a set of TAGs (e.g., SOP_INSTANCE_UID (0008,0018), SERIES_INSTANCE_UID (0020,000E), PATIENT_ID (0010,0020)), already known to FIS 40, which instruct the FIS to send data.

Bundled in the value field of the TAGs in the C_MOVE command are unique identifiers (UID). The UIDs specify whether CTS 20 is requesting a regular fluoroscopic image (e.g., without file size reduction with dummy payload), or real time fluoroscopic gantry position data (e.g., with a dummy payload), or any other suitable data. When CTS 20 sends C_MOVE command to FIS 40 over network 210, FIS processor 240 identifies from the UIDs if data is to be sent to CTS 20 over network 210 requires file size reduction with a dummy payload.

FIS 40 then opens a second association with CTS 20, while the first association is open, and starts to send C_STORE messages. C_STORE DICOM command (e.g., message) comprises a set of TAGs with the requested data to CTS 20. When the C_MOVE UIDs comprise a request for the real time position of gantry 44, FIS processor 240 bundles the dummy 1×1 pixel image into the appropriate C_STORE TAG fields. FIS 40 then sends updates to CTS 20 about any changes in the orientation of gantry 44 in the C_STORE DICOM messages, such as changes in the X-ray source (e.g, fluoroscope 42) to image-intensifier distance (SID), geometry information as table 19 moves or rotates, etc.

When CTS 20 no longer requires the real time messages from FIS 40, CTS 20 closes or cancels the first association (e.g., for C_MOVE) with FIS 40. In response to this, FIS 40 automatically closes the second association (e.g., C_STORE). All communication between FIS 40 and CTS 20 is thus terminated.

In the embodiments described above, the first and second associations between FIS 40 and CTS 20 remain open for the duration of the medical session. FIS 40 periodically sends fluoroscope position updates to CTS 20. However in alternative embodiments, CTS 20 may request FIS 40 to operate in a burst mode. In a burst mode, FIS 40 transmits fluoroscope position updates over network 210 as the gantry position changes, or in response to some other event, as needed and not necessarily at periodic intervals. Since the associations remain open, CTS processor 220 is configured to use the gantry position updates when received by CTS 20.

Figure 3:
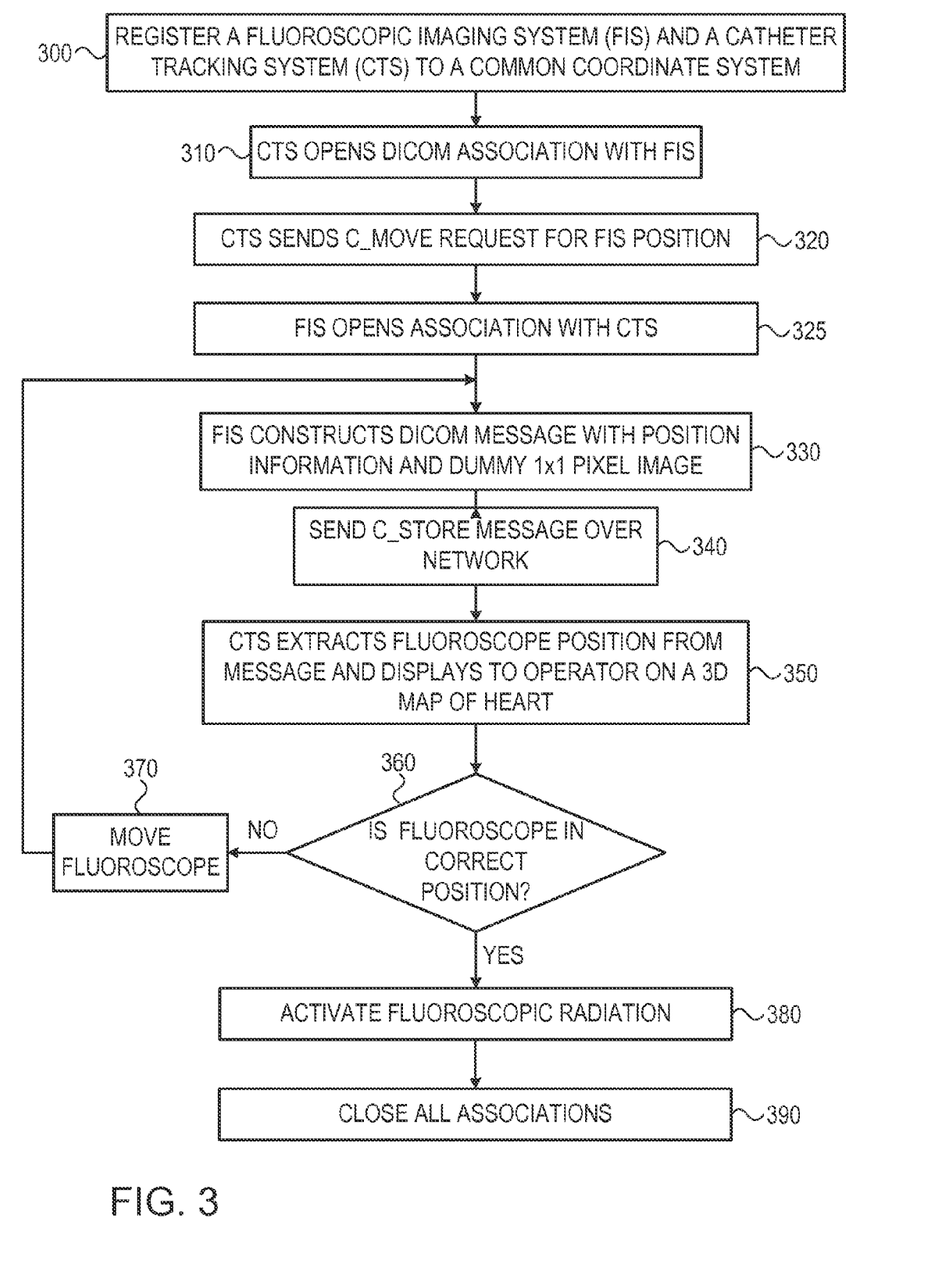
FIG. 3 is a flow chart that schematically illustrates a method for assessing a position of a fluoroscope during a medical procedure, in accordance with an embodiment of the present invention.

FIG. 3 is a flow chart that schematically illustrates a method for assessing a position of a fluoroscope during a medical procedure, in accordance with an embodiment of the present invention. The embodiment described in the flowchart of FIG. 3 is for CTS 20 and FIS 40 communicating in a burst mode, where FIS 40 sends the C_STORE tags in one or more bursts while the associations are open.

In a registering step 300, fluoroscopic imaging system (FIS) 40 and catheter tracking system (CTS) 20 are registered to a common coordinate system. In an opening step 310, CTS 20 opens a DICOM association with FIS 40 over network 210. In this DICOM association, in which the CTS requests a move operation from the FIS, the CTS serves as the Service Class User (SCU) and the FIS serves as the Service Class Provider (SCP). In a requesting step 320, CTS 20 sends a C_MOVE request for the position of fluoroscope 42 in FIS 40 (e.g., with the appropriate UIDs indicating real time data in the C_MOVE value fields).

In a second opening step 325, FIS 40 opens an association with CTS 20. In this DICOM association, in which the FIS sends the data to the CTS as a client to a server, the FIS serves as the SCU and the CTS serves as the SCP. In a constructing step 330, FIS 40 (e.g., FIS processor 240) constructs a DICOM message with FIS position information and a dummy 1×1 pixel image. In a sending step 340, processor 240 sends a DICOM C_STORE message over network 210 using interface 250.

In an extracting step 350, CTS 20 (e.g., CTS processor 220) receives the DICOM message via interface 230, extracts the position of fluoroscope 42 from the message and displays the position to operator 70 on a 3D map of the heart on display 50.

In a decision step 360, CTS processor 220 assesses if fluoroscope 42 is in the correct position. If not, in a moving step 370, fluoroscope 42 is moved (manually or automatically) and an updated DICOM C_STORE message is constructed in constructing step 330. In this manner (e.g., in burst mode), the FIS does not require a separate request for each position report. The FIS may send a sequence of multiple C_STORE messages in response to the C_MOVE request, each comprising a respective position of the fluoroscope, in response to a single request.

If fluoroscope 42 is in the correct position, fluoroscope 42 in FIS 40 is activated in an activating step 380 so as to acquire the fluoroscopic image. In a closing step 390, all associations are then closed. (e.g., at the end of the medical session).

Although the embodiments described herein mainly address fluoroscopic imaging, the methods and systems described herein can also be used in other imaging equipment communicating over a network, and generally to communicate between any other suitable kinds of medical devices.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   sending over a network from a first medical device to a second medical device a request for data using a non-real-time communication protocol that comprises messages for conveying medical measurement results; and
   in response to the request, producing in the second medical device at least one message that comprises the requested data and a dummy payload instead of the medical measurement results, and sending over the network the at least one message from the second medical device to the first medical device using the communication protocol;
   wherein at least one network association between the first and second medical devices is opened when the first medical device sends the request to the second medical device and is closed when the network association is terminated by the first medical device;
   wherein sending the at least one message comprises sending the data in multiple messages in response to the request while the at least one association is open; and
   wherein the medical measurement results comprise an image, and wherein the dummy data comprises a dummy image.

2. The method according to claim 1, wherein sending the request comprises opening at least one association between the first medical device and the second medical device, and wherein sending the at least one message comprises sending the data in one or more bursts while the at least one association is open.

3. The method according to claim 1, wherein the communication protocol comprises a Digital Imaging and Communications in Medicine (DICOM) protocol.

4. The method according to claim 1, wherein the first medical device comprises a position tracking system.

5. The method according to claim 1, wherein the second medical device comprises a fluoroscopic imaging system.

6. The method according to claim 1, wherein the first medical device comprises a position tracking system, wherein the second medical device comprises a fluoroscopic imaging system, and wherein sending the at least one message comprises sending one or more messages that report respective spatial positions of the fluoroscopic imaging system.

7. The method according to claim 6, and comprising presenting the reported positions of the fluoroscopic imaging system to an operator, using the position tracking system, without activating the fluoroscopic imaging system.

8. The method according to claim 6, and comprising compensating, based on the reported positions, for a distortion caused by the fluoroscopic imaging system to a magnetic field of the position tracking system.

9. A system, comprising:
   a first medical device, which is configured to send over a network a request for data using a non-real-time communication protocol that comprises messages for conveying medical measurement results; and
   a second medical device, which is configured to produce, in response to the request, at least one message that comprises the requested data and a dummy payload instead of the medical measurement results, and to send over the network the at least one message to the first medical device using the communication protocol;
   wherein at least one network association between the first and second medical devices is opened when the medical session is initiated, and is closed when the network association is terminated by the first medical device;
   wherein the second medical device is configured to send the data in multiple messages in response to the request while the at least one association is open; and
   wherein the medical measurement results comprise an image, and wherein the dummy data comprises a dummy image.

10. The system according to claim 9, wherein the first and the second medical devices are configured to open at least one association between the first medical device and the second medical device upon sending the request, and wherein the second medical device is configured to send the data in one or more bursts while the at least one association is open.

11. The system according to claim 9, wherein the communication protocol comprises a Digital Imaging and Communications in Medicine (DICOM) protocol.

12. The system according to claim 9, wherein the first medical device comprises a position tracking system.

13. The system according to claim 9, wherein the second medical device comprises a fluoroscopic imaging system.

14. The system according to claim 9, wherein the first medical device comprises a position tracking system, and wherein the second medical device comprises a fluoroscopic imaging system that is configured to send, in response to the request, one or more messages that report respective spatial positions of the fluoroscopic imaging system.

15. The system according to claim 14, wherein the position tracking system is configured to present the reported positions of the fluoroscopic imaging system to an operator, without activation of the fluoroscopic imaging system.

16. The system according to claim 14, wherein the magnetic position tracking system is configured to compensate, based on the reported positions, for a distortion caused by the fluoroscopic imaging system to a magnetic field of the position tracking system.

* * * * *